United States Patent [19]

Cornely et al.

[11] 3,997,618

[45] Dec. 14, 1976

[54] PROCESS FOR ISOMERIZING ALKYL BENZENES

[75] Inventors: Kurt W. Cornely, Westfield; Saul G. Hindin, Mendham; Carl D. Keith, Summit, all of N.J.

[73] Assignee: Engelhard Minerals & Chemicals Corporation, Murray Hill, N.J.

[22] Filed: May 23, 1975

[21] Appl. No.: 580,446

Related U.S. Application Data

[63] Continuation of Ser. No. 21,520, March 20, 1970, abandoned.

[52] U.S. Cl. ............................................. 260/668 A
[51] Int. Cl.² ........................................... C07C 5/24
[58] Field of Search ............................... 260/668 A

[56] References Cited

UNITED STATES PATENTS 3,632,835   1/1972   Mitsche et al. ................ 260/668 A

*Primary Examiner*—C. Davis

[57] ABSTRACT

There is disclosed a process for isomerizing alkylated benzenes having from 3–10 carbon atoms and methyl or ethyl alkyl substituents. The reaction is conducted in the presence of molecular hydrogen and a catalyst having a platinum group metal, especially platinum, and rhenium promoters on a porous, solid oxide, acidic support. The support can be a mixture of a low acidic material such as alumina, and a higher acidic material such as silica-alumina or crystalline aluminosilicate. The catalyst promoters are preferably supported on the low acidity base component.

12 Claims, No Drawings

PROCESS FOR ISOMERIZING ALKYL BENZENES

This is a continuation of application Ser. No. 21,520, filed Mar. 20, 1970, and now abandoned.

The present invention relates to a process for isomerizing alkylated benzene hydrocarbons having from 8–10 carbon atoms and whose alkyl substituents are methyl or ethyl groups or their combinations. In this invention the isomerization is effected in the presence of hydrogen and by contact of the feed hydrocarbon with a catalyst containing a platinum group metal, rhenium and a porous, solid oxide of substantial acidity. The performance of the catalyst in this reaction system is especially advantageous in not only that the catalyst exhibits high isomerization activity over a considerable processing time but, in addition, the catalyst permits the use of relatively lower pressures and temperatures in the reaction while obtaining a given approach towards a product having an equilibrium mixture of feedstock isomers. Such less severe reaction conditions afford relatively lower yields of by-products having a lesser number of carbon atoms than the feed hydrocarbons, while the approach to equilibrium is high, for instance at least about 95% accomplished.

There is substantial interest in the isomerization of alkylated benzenes of 8–10 carbon atoms and having two or more alkyl substituents which are either methyl or ethyl radicals. These feed materials are especially exemplified by the xylenes, particularly hydrocarbon mixtures rich in meta-xylene and having less than an equilibrium amount of para-xylene and often a minor amount of ethylbenzene. During the isomerization the meta-xylene-rich feeds are converted to reaction products containing greater amounts of para-xylene, the latter isomer being separable from the reaction product as by crystallization or extraction and employed after oxidation, in the manufacture of polymers. The product may also be reduced in ethylbenzene content compared with the feed. Other suitable feedstocks include psuedocumene, prehnitene, etc., and the various alkylated benzenes are usually available in forms containing less than about 10 ppm by weight sulfur, often less than about 1 ppm. One example of this type of isomerization is described in U.S. Pat. No. 2,976,332, whose process employs a catalyst containing a platinum on alumina component which is physically mixed with a silica-alumina cracking component. In the operation, the feed hydrocarbons which have a non-equilibrium amount of its isomers taken on the basis of their ratio that would be present in thermodynamic equilibrium at the isomerization temperature, are converted to a mixture of isomers more closely approximating their equilibrium amounts. If desired, a selected isomer or mixture of isomers can be separated from the product and remaining materials recycled to the reaction zone for isomerization along with fresh alkylated benzene feedstock.

As previously stated, the present invention is directed to the foregoing described alkylated benzene isomerization systems, but is materially improved by the use of a catalyst containing platinum group metal, rhenium and a porous, solid oxide exhibiting substantial acidity. Although it is preferred that the catalyst be a physical admixture of particles in which the platinum group metal and rhenium are supported on a porous, solid oxide base of relatively low, if any, acidity, for instance, alumina, with particles of a porous, solid oxide exhibiting substantial acidity but low in hydrogenation-dehydrogenation activity, e.g., silica-alumina, crystalline aluminosilicates of relatively large pore size or their mixtures; other forms of the catalyst can be employed. Thus, either the platinum group metal or rhenium promoter can be disposed on the relatively non-acidic, oxide support while the other of the platinum group metal or rhenium promotor is carried by the oxide base of higher acidity. Also, all of the catalyst support or base components can be mixed to form a composite on which the platinum group metal and rhenium are then deposited. In another alternative form of the catalyst, both the platinum group metal and rhenium promoters can be disposed on the oxide base component of substantial acidity and then the composite physically mixed with a solid, porous oxide of low acidity to give an overall catalyst having the desired acidity. In the latter type of catalyst, the acidic support may be a mixture of silica-aluminas with the platinum group metal and rehnium being on both or separate ones of the silica-alumina particle types. For instance, it can be advantageous if the platinum group metal is supported on silica-alumina containing about 10 to 20 weight % alumina while the rhenium is supported on silica-alumina having an alumina content of about 25 to 40 weight %.

The catalyst employed in the method of this invention has an overall or average basis, minor amounts of the platinum group metal and rhenium. Thus, each of these types of promoters may often be about 0.1 to 2.5 weight % of the overall catalyst, preferably each being about 0.2 to 1 weight %. Although various platinum group metals can be used in the catalyst, for instance, platinum, palladium, rhodium, etc., platinum is preferred.

The major portion of the catalyst employed in the isomerization process of this invention is the solid, porous oxide. The total oxide can be about 95 to 99.8 weight %, although it can be a lesser portion of the catalyst, but usually at least about 90 weight %, as the result of the presence of materials other than the platinum-group metal and rhenium promoters. The platinum-group metal and rhenium promoters can, and preferably are, in elemental state when the catalyst is used in the reaction, however, the promoters may also be in combined form such as their oxides or sulfides. It is preferred that the platinum group metal and rhenium in the catalysts are not detectable by X-ray diffraction analysis which means that if the metals be present in the elemental state, their crystallite sizes are less than about 50 A as determined by X-ray techniques.

One method of providing the platinum group metal in the catalyst is by contact of the support, either in hydrous or in calcined form, with an aqueous solution of a halogen-containing compound, for instance chloroplatinic acid. In this manner, halogen is incorporated in the catalyst, for instance, in amounts of about 0.2 to 2 weight %, preferably about 0.3 to 1 weight %. Such amounts of halogen, e.g. chlorine, component can also be provided in the catalyst from a source other than the compound supplying the platinum group metal. Rhenium can also be added to the hydrous or calcined support through contact with an aqueous solution of rhenium compound, e.g. perrhenic acid or ammonium perrhenate. If promoting metal is added to a calcined support, the resulting composite is generally recalcined. Calcination of the catalysts used in this invention can be conviently conducted at temperatures of the order of about 700° to 1200° F., or more, for instance in an oxygen-containing gas, and this operation can be controlled to give a final catalyst of desired surface area.

The catalyst employed in the isomerization process of this invention has an overall, solid, porous oxide or base component which, as previously indicated, exhibits substantial acidity, i.e., having a tertiary butylbenzene dealkylation activity of at least about 20 cubic centimeters (STP) per gram per minute at 455° C., as measured, without water addition by the method of Marvin F. L. Johnson and John S. Melik, "Dealkylation of t-Butylbenzene by Cracking Catalysts", Journal of Physical Chemistry, Vol. 65, pp. 1146–1150 (1961), preferably, such activity is about 400 to 1200. At the various places in this specification that reference is made to tertiary butylbenzene dealkylation activity such is indicated as measured by this test published by Johnson and Malik.

The oxides which make up this base component of the catalyst are of selected characteristics in order to provide the desired acidity and generally with low hydrogenation-dehydrogenation activity. The porous oxide component is usually comprised of a mixture of metal oxides, the metals of which are often selected from Groups II to IV of the periodic chart. Examples of such metal oxides are silica, alumina, titania, zirconia, magnesia, clays, and synthetic and natural amorphous or crystalline aluminosilicates, and their mixtures. It is especially preferred that the catalyst base contain both silica and alumina in some form, especially in the oxide component of relatively high acidity. Also, the catalyst may have minor amounts of non-metal components, especially those which enhance acidic activity such as boria and the halogens, for instance, fluorine and chlorine.

Most advantageously, the catalyst of the present invention contains a mixture of metal oxides of more or less distinct types, that is, a relatively low acidity oxide component exhibiting a tertiary butylbenzene dealkylation activity of up to about 15, preferably up to about 10, along with a relatively high acidity oxide component having a tertiary butylbenzene dealkylation activity of at least about 30, preferably at least about 500. The amounts of these separate oxide components present in the catalyst are such as to give an overall porous oxide mixture of desired acidity, often about 10 to 90 weight % of each. The relatively high acidity component can be about 0.5 to 95 weight % of the catalyst, preferably about 10 to 70 weight %. For example, the total catalyst base may contain about 30 to 95 weight % of amorphous silica-alumina, preferably about 40 to 70 weight %, with the essential balance of the base being composed of the relatively non-acidic or low activity component, for instance, alumina. As another example, the overall porous oxides of the catalyst can be composed of 1 to 50 weight %, preferably about 10 to 30 weight %, of an acidic catalyst material containing a mixture of crystalline aluminosilicate and amorphous silica-alumina in which the crystalline aluminosilicate is about 5 to 25 weight % and the essential remaining portion of the overall base oxides is essentially a lower activity material such as alumina. As a further alternative the catalyst base can contain about 0.5 to 40 weight %, preferably about 10 to 25 weight % of a crystalline aluminosilicate, with the essential balance of the porous oxides being alumina.

The various porous oxide materials which can be included in the catalyst of the present invention are available in many forms. These oxides are generally of relatively high surface area and exhibit a BET surface area as determined by the nitrogen absorption method (JACS), Volume 60, beginning at page 309 (1938), of at least about 100 square meters per gram, preferably about 200 to 600 or even about 900 or more square meters per gram. As a relatively low acidity catalyst component, alumina is particularly preferred and it can be in one or a mixture of the activated forms known as gamma family aluminas such as chi, gamma and eta aluminas.

An alumina component which can be present in the catalyst used in the method of the present invention often has a surface area of at least about 150 square meters per gram and is preferably composed to a major extent of gamma-family alumina modifications derived by the activation or calcination of alumina trihydrates. These gamma-family or activated alumina modifications include among others, gamma and eta aluminas. U.S. Pat. No. 2,838,444 discloses this type of alumina support having surface areas in the range of about 350 to 550 square meters per gram, while in U.S. Pat. No. 2,838,445 there is described catalyst supports made from predominantly trihydrate alumina precursors, the supports having surface areas in the range of about 150 to 350 square meters per gram. These supports are suitable for use in the present invention, especially the higher area supports of U.S. Pat. No. 2,838,444 which supports during use may have their surface areas reduced to, for instance, about 150 to 250 square meters per gram. As stated, the preferred alumina precursors predominate in trihydrate which may contain one or more of the bayerite, gibbsite or nordstrandite (previously called randomite) forms, and preferably a major amount of the trihydrate is composed of bayerite or nordstrandite which when calcined can form eta alumina. It is also advantageous that the hydrous alumina precursor contain about 65 to 95% of the trihydrate with the essential balance being composed of one or both of the alumina monohydrate, boehmite, or amorphous hydrous alumina. Preferred alumina support components have pore volumes of at least about 0.1 cc./gm.; preferably at least about 0.15 cc./gm., in pores greater than about 100 A radius. It is also preferred that these support materials have at least about 0.05 cc./gm., in pores greater than about 300 A or even greater than about 600 A radius. These determinations are by the method described by Barrett, Joyner and Halenda, JACS, 73 p. 373 (1951).

The amorphous silica-alumina which can be present in the catalyst employed in the method of this invention is available in several forms. These materials usually contain about 10 to 40 weight % alumina with the essential balance being silica, although minor amounts of other components such as metal oxides may be present. These silica-aluminas after calcination often have surface areas of about 100 to 500 square meters per gram.

Other types of silica-alumina material which can be in the catalyst of the present invention are the natural and synthetic crystalline aluminosilicates. These materials are of the relatively large pore variety, that is, having relatively uniform pore openings with a minimum diameter of about 10 A, for instance, 10 to 15 A, preferably 12 to 14 A. The mole ratio of silica-to-alumina in these crystalline materials is at least about 2:1, say up to about 12:1 or more, however, the preferred crystalline aluminosilicates have silica-to-alumina mole ratios of about 2 to 6:1, or even about 4 to 6:1, such as those of the faujasite type. The various crystalline aluminosilicates are usually available or made in the sodium form and generally it is desired to reduce the sodium content of these materials so that it is less than about 4 weight % or even less than about 1 weight % of the crystalline aluminosilicate. The amount of sodium can be reduced through exchange with hydrogen ions, or precursors thereof such as ammonium ions, or with polyvalent metal ions, for instance, those of the rare earth series such as cerium, praseodymium, etc., or their mixtures. Often, the extent of ion exchange is such that at least about 50 mole %, preferably at least about 90 mole %, of the sodium is removed.

The isomerization process of this invention can be carried out at temperature of about 650 to 950° F., preferably about 700 to 900° F. Other suitable reaction conditions include pressures of about 50 to 500 psig, space velocities of about 0.2 to 20, WHSV (weights of hydrocarbon per weight of catalyst per hour) and at molecular hydrogen to hydrocarbon mol ratios of 3 3 to 30:1. Preferably, these reaction conditions are about 100 to 350 psig, about 0.5 to 15 WHSV and about 4 to 15:1 hydrogen to hydrocarbon mole ratio. Preferably, the fluid materials in the isomerization reaction zone have less than about 100 ppm sulfur, preferably less than about 20 ppm or even less than about 10 ppm.

In the reaction system of the present invention the catalysts can be employed in any convenient particle size. Thus, the catalyst may be finely divided and employed as fluidized bed, but more preferably the catalyst is macrosize size as obtained, for instance, by tabletting or extrusion. The macrosize particles usually have diameters of about 1/64 to ¼ inch, preferably about 1/32 to ⅛ inch and, if not spherical, lengths of about 1/64 to one inch or more, preferably about ⅛ to ¾ inch. The macrosize catalyst can be employed as a fixed or moving bed and more often is used as a fixed bed in the reaction zone.

Carbonaceous deposits can accumulate on the catalysts of this invention as isomerization proceeds, and the catalysts can be regenerated by carbon burn-off which improves the catalytic characteristics sufficiently for the catalysts to be reused on an economic basis. At the beginning of regeneration, the carbon content of the catalysts is generally above about 0.5 weight %, often greater than about 3 weight %. During regeneration of the catalysts by burning, the carbon level is often reduced to below about 0.5 weight %, preferably below about 0.2 weight %. This burning can be conducted through contact of the catalysts with an oxygen-containing gas and generally the amount of oxygen is controlled to maintain the temperature of the catalysts from about 700° to about 400° or 1000° F., preferably in the temperature range of about 700° to 850° F. The pressure maintained during burning is preferably elevated, for instance, is about 50 to 500 psig. The controlled burning is usually initiated with an inert gas, e.g. nitrogen, carbon dioxide or their mixtures, containing a small amount of oxygen, for instance, up to about 1 mole % and preferably with an oxygen partial pressure of at least about 0.2 psig. When the bulk of the carbon has been removed from the catalysts by a gas containing the relatively low concentration of oxygen, the amount of oxygen can be increased somewhat to insure that sufficient carbon has been removed from the catalysts without exceeding the desired temperature. This type of treatment is exemplified by one or more burns-through of a fixed catalyst bed at about 800° F., to 850° F., and about 100 to 500 psig, with a gas containing above about 1 to 3 or somewhat greater mole percent oxygen. Other suitable carbon-burning procedures can be employed as long as the temperatures are controlled and the carbon level of the catalysts is adequately lowered. During carbon burn-off and any subsequent treatments of the catalysts with an oxygen-containing or other gas at elevated temperatures, the gas should be dry enough to avoid undue sintering of the catalysts and loss of surface area. Such loss generally increases as temperature, water content of the gas or treating time is raised.

Especially where the crystallite size of the promoting metals on the catalysts is to be reduced, the catalysts can, after carbon burn-off, be contacted with an oxygen-containing gas at a temperature of about 800 to 1000° F., preferably about 850° to 950° F., and, if desired, an elevated pressure such as about 100 to 500 psig. This treatment can be referred to as an air soak and the oxygen content of the gas is usually greater than that present in the gas employed for carbon burn-off. Thus, the oxygen content of the gaseous stream employed for air soaking is often at least about 5 mole % with there having been found no particular reason for increasing the gas content above about 20 mole %. The air soaking period is generally at least about one hour and is usually continued for several hours, for instance, in the range of about 5 to 24 hours. Regeneration and air soaking procedures suitable for the catalysts of the present invention are disclosed in U.S. Pat. No. 2,922,756, herein incorporated by reference.

The virgin catalysts of this invention or used catalysts, of such types, say after regeneration with or without reactivation, can be reduced by contact with a gaseous stream which contains molecular hydrogen. The treatment can be at an elevated temperature, for instance, about 600° to 1000° F., preferably about 750° to 950° F. Elevated pressures are preferably used in the reduction and can be, for example, about 20 to 600 psig, preferably about 50 to 350 psig. Apparently, the reduction converts the catalytic promoting metals to their elemental state, but if a vaporous sulfiding agent be present some or all of the promoting metals may be sulfided. The gas stream employed during reduction is often composed of about 70 to 100 volume % hydrogen, preferably about 95 to 99 to 100 volume %, with any remaining components being up to about 30 volume % of inert gas such as nitrogen. The gas advantageously contains less than about 1 volume % hydrocarbons boiling above methane, preferably less than about 0.1%.

To avoid undue hydrocracking of the hydrocarbon feedstock during the initial period of hydrocarbon processing after the catalysts of the present invention are placed on-stream, the catalysts can be contacted with a gas containing sulfur-providing component in vaporous form. This sulfiding treatment can be conducted simultaneously with or subsequent to the reduction. If sulfiding is conducted simultaneously with the reduction, a non-carbonaceous sulfur compound is preferably used due to the presence of oxygen in the system and to avoid any localized over-heating of the catalyst. A suitable sulfur-providing material or sulfiding agent is $H_2S$. The amount of sulfiding agent employed is at least about 25% or even at least about 50% of the stoichiometric amount needed to give one atomic weight of sulfur for each atomic weight of total platinum group metal and rhenium is the catalyst, preferably the amount is at least about 50% to say up to about 500% or more. The sulfiding operation can be done at an elevated temperature, e.g. about 650 to 950° F., and at any suitable pressure, preferably an elevated pressure such as about 100 to 500 psig. The sulfiding gas is reductive and usually contains a minor amount of the sulfur-bearing component, e.g. about o.1–10 volume %, preferably about 0.2 to 3%, with the major component being hydrogen or an inert gas such as nitrogen. When the sulfiding is conducted simultaneously with or subsequent to reducing the catalysts with hydrogen, the catalysts are in sulfided form when they first contact the hydrocarbon being processed which avoids excessive hydrocracking with its attendent yield and selectivity losses.

It can be further advantageous in minimizing hydrocracking caused by the reduced catalysts whether presulfided or not, to supply vaporous sulfiding agent to the conversion system when charging of the hydrocarbon feedstock is begun. Thus, a small amount of the sulfiding agent, sufficient to significantly reduce hydrocracking during the initial portion of the processing cycle, can be added to the system. The sulfiding agent can conveniently be charged with the recycle or with the hydrocarbon stream. The amounts of sulfiding agent employed include about 1 to 500 ppm by volume based on the hydrogen passing to the reaction system, preferably about 5 to 200 ppm. This sulfiding-agent addition can be continued as long as the operator desires but often the addition will approximate the time period in which, in the absence of the sulfiding-agent addition, the catalysts would cause significantly excessive hydrocracking. The period of sulfiding-agent addition upon placing the reduced catalysts back on processing can include, for instance, about 1 to 60 or more days and is often about 3 to 10 days.

It may also be advantageous to incorporate in the reaction system a small amount of ammonia or a material which is decomposed under the reaction conditions to supply ammonia such as the lower alkyl amines, for instance, butyl amine. The ammonia can serve to give better catalyst performance during an initial period of relatively high activity in order that the desired selectively can be obtained, for instance, an approach of at least about 95% towards equilibrium. The amount of ammonia is often about 5 to 200 parts per million by weight based on the alkylated benzene feed, preferably about 10 to 100 parts per million. As the reaction proceeds it may be necessary to decrease the amount of ammonia and to even omit its introduction entirely in order to obtain an adequate approach to equilibrium. It may be advantageous to enhance the activity of the system by providing about 5 to 200 ppm water based on the weight of the alkylated benzene feed, preferably about 25 to 75 ppm. The water may be especially desired when the overall porous oxides of the catalyst have a tertiary butylbenzene dealkylation activity of below about 30.

The following catalysts are evaluated in the isomerization of xylenes

Catalyst A — This catalyst is a physical admixture of spray-dried alumina having impregnated therein 0.6% platinum and 0.6% rhenium (calcined basis), the alumina, whose t-butylbenzene dealkylation activity is 13, being a mixture of 45% bayerite,
10% gibbsite,
20% nordstrandite,
22% boehmite and 3% amorphous hydrous alumina; with about an equal amount by weight (on a ignited weight basis) of spray-dried, microspherical, amorphous silica-alumina cracking catalyst containing about 12 weight % alumina and after partial deactivation and calcination having a t-butylbenzene dealkylation activity of about 1600. The mixture, containing sufficient water to provide an extrudable consistency, is extruded, into particles 1/16 inch in diameter and about ¼ to ¾ inch in length. The extruded particles are dried and then calcined in a stream of dry air at 900° F. for three hours. The calcined particles have a surface area of about 400 square meters per gram, and a calcined composite of the porous oxides in the catalyst, that is, on a non-platinum, non-rhenium basis, exhibits a t-butylbenzene dealkylation activity of about 800.

Catalyst B — This catalyst is made by impregnating a spray-dried alumina containing about 75% bochmite having a crystallite size of 35 A., and about 25% amorphous hydrous alumina with 0.7% platinum and 0.5% rhenium (calcined basis). The impregnated alumina (t-butylbenzene dealkylation activity of 5) is mixed with 25% based on the total ignited weight of an ammonium-exchanged, crystalline aluminosilicate of the faujasite type having a silica-to-alumina mole ratio of 4.5:1 and pore openings of 13 A diameter. The mixture is combined with water to give a material of extrusion consistency and is extruded into particles of the same size as those of Catalyst A. These particles are calcined in the manner of Catalyst A and the calcined catalyst has a surface area of about 375 square meters per gram. The composite porous oxides of the catalyst, that is on a non-platinum, non-rehenium basis, has a t-butylbenzene dealkylation activity of about 1000 after calcination.

Each of catalysts A and B is evaluated in the isomerization of xylenes. The catalyst is disposed in the reactor as a fixed bed and is prereduced in hydrogen at about 900° F. The xylene feedstock contains about 7 weight % para-xylene, 46 weight % meta-xylene, 38 weight % ortho-xylene, 5% ethylbenzene, 4% total paraffins and cyclo-parafins and essentially no sulfur. The isomerizations are conducted at about 820° F., 175 psig, 2 WHSV and 5:1 hydrogen to hydrocarbon mole ratio. Both catalysts A and B when used in the isomerization system give an approach to equilibrium in the range of about 95 to 98% and the product contains less than 4 weight % increase in hydrocarbons boiling below the $C_8$ range. The catalyst also exhibits good life and relatively low coke formation during the isomerization.

It is claimed:
1. A process for isomerizing alkylated benzene hydrocarbons of 8 to 10 carbon atoms wherein the alkyl substituents are selected from the group consisting of methyl and ethyl groups, which comprises isomerizing such alkylated benzene hydrocarbons in the presence of molecular hydrogen under isomerization conditions including a temperature of about 650° to 950° F and in contact with a catalyst, said catalyst consisting essentially of a physical admixture of a. minor amounts each of platinum group metal and rhenium supported on a major amount of a porous, solid metal oxide base, said base having a surface area of at least about 100 square meters per gram and having a tertiary butylbenzene dealkylation activity at 455° C (without water addition) of up to about 15 cubic centimeters (STP) per gram per minute; and b. 0.5 to 95% of a high acidity oxide component consisting essentially of a porous, solid metal oxide having a surface area of at least about 100 square meters per gram and having a tertiary butylbenzene dealkylation activity of at least about 500, wherein the physical admixture has a tertiary butylbenzene dealkylation activity of about 400 to 1200.

2. The process of claim 1 in which the platinum group is metal is platinum.

3. The process of claim 1 in which the base of relatively low activity is alumina and the metal oxide of relatively high activity is amorphous silica-alumina.

4. The process of claim 1 in which the platinum group metal is platinum and each of the platinum and rhenium is about 0.2 to 1% of the catalyst.

5. The process of claim 1 in which the relatively low activity base is alumina, and the metal oxide of relatively high activity is crystalline aluminosilicate having a silica-to-alumina mole ratio of about 2 to 6:1, pore openings of 10 to 15 A diameter and a sodium content below about 1%.

6. The process of claim 5 in which the platinum group metal is platinum.

7. The process of claim 2 in which the alkylated benzene feed is a xylene mixture containing meta-xylene and less than an equilibrium amount of para-xylene.

8. The process of claim 4 in which the alkylated benzene feed is a xylene mixture containing meta-xylene and less than an equilibrium amount of para-xylene.

9. The process of claim 7 in which the isomerization conditions include about 700 to 900° F. and about 100 to 350 psig.

10. The process of claim 8 in which the isomerization conditions include about 700 to 900° F. and about 50 to 500 psig.

11. The process of claim 9 in which the alumina of the catalyst is made by calcination of a hydrous alumina predominating in trihydrate.

12. The process of claim 10 in which the alumina of the catalyst is made by calcination of a hydrous alumina predominating in trihydrate.

* * * * *

UNITED STATES PATENT OFFICE
CERTIFICATE OF CORRECTION

Patent No. 3,997,618          Dated December 14, 1976

Inventor(s) Kurt W. Cornely, et al.

It is certified that error appears in the above-identified patent and that said Letters Patent are hereby corrected as shown below:

Column 1, line 41, "psuedocumene" should read -- pseudocumene --.

Column 2, line 28, after the word "has" insert -- on --.
Column 2, line 68, "conviently" should read -- conveniently --
Column 5, line 23, "mol ratios of 3 3 to" should read -- mol ratios of about 3 to --.

Column 5, line 18, "temperature" should read -- temperatures --.

Column 5, line 56, "from about 700° to about 400°" should read

-- from about 700° to about 900° --.

Column 6, line 5, after the word "to" insert the word -- about --.
Column 6, line 49, "about 95 to 99 to 100" should read -- about 95 or 99 to 100 --.

Column 7, line 3, "is" should read -- in --.

Column 7, line 27, after "recycle" insert the word -- gas --.

UNITED STATES PATENT OFFICE
CERTIFICATE OF CORRECTION

Patent No. 3,997,618          Dated December 14, 1976

Inventor(s) Kurt W. Cornely, et al,

It is certified that error appears in the above-identified patent and that said Letters Patent are hereby corrected as shown below:

Column 8, line 4, "(on a ignited" should read -- (on an ignited --.

Column 8, line 21, "bochmite" should read -- boehmite --.

Column 8, line 28, "faujasitc" should read -- faujasite --.

Column 8, line 36, "rehenium" should read -- rhenium --.

Column 9, line 12, delete the first occurrence of the word "is".

Column 9, line 18, "rehenium" should read -- rhenium --.

Signed and Sealed this twenty-third Day of August 1977

[SEAL]

Attest:

RUTH C. MASON
*Attesting Officer*

C. MARSHALL DANN
*Commissioner of Patents and Trademarks*